US005119467A

United States Patent [19]
Barsky et al.

[11] Patent Number: 5,119,467
[45] Date of Patent: Jun. 2, 1992

[54] TRANSPARENT FILM RADIANT HEAT SOURCE FOR USE WITH INCUBATORS

[75] Inventors: Barry E. Barsky, Huntingdon Valley; Joseph P. Bagnell, Southampton; Jan F. Wenstrup, Doylestown, all of Pa.

[73] Assignee: Air-Shields, Inc., Hatboro, Pa.

[21] Appl. No.: 561,893

[22] Filed: Aug. 2, 1990

[51] Int. Cl.⁵ .......................... A61G 11/00; H05B 3/34
[52] U.S. Cl. ........................................ 392/439; 219/543; 338/308; 600/22; 119/37
[58] Field of Search ............... 219/543, 203, 411, 405; 338/308-309; 600/22; 237/3, 14; 236/2, 3; 119/37; 392/407, 435, 438, 439

[56] References Cited

U.S. PATENT DOCUMENTS

| | | | |
|---|---|---|---|
| 1,245,829 | 11/1917 | Vance | 119/37 |
| 2,358,081 | 9/1944 | Marick | 392/438 |
| 2,523,353 | 9/1950 | Boester | 392/438 |
| 2,535,393 | 12/1950 | Daugert | 392/438 |
| 2,579,964 | 12/1951 | Reynolds | 392/438 |
| 3,180,781 | 4/1965 | Ryan et al. | 219/203 |
| 3,299,253 | 1/1967 | Lawson, Jr. | 219/385 |
| 3,655,545 | 4/1972 | Gillery et al. | |
| 3,718,535 | 2/1973 | Armstrong et al. | 219/203 |
| 3,858,570 | 1/1975 | Beld et al. | |
| 3,878,361 | 4/1975 | Levin et al. | 219/203 |
| 3,898,427 | 8/1975 | Levin et al. | |
| 3,974,359 | 8/1976 | Orcutt et al. | |
| 4,034,740 | 7/1977 | Atherton et al. | 236/3 |
| 4,206,615 | 6/1980 | Sabajima et al. | |
| 4,459,470 | 7/1984 | Shlichta et al. | |
| 4,707,586 | 11/1987 | Voss et al. | |
| 4,743,741 | 5/1988 | Ramus. | |
| 4,786,783 | 11/1988 | Woodward. | |
| 4,820,902 | 4/1989 | Gillery. | |

FOREIGN PATENT DOCUMENTS

| | | | |
|---|---|---|---|
| 1251540 | 12/1960 | France | 219/385 |
| 2196781 | 3/1974 | France | |
| 812871 | 5/1959 | United Kingdom | 119/37 |
| 1092164 | 11/1967 | United Kingdom | |
| 1546734 | 5/1979 | United Kingdom. | |

OTHER PUBLICATIONS

Agate, Frederick J.; Silverman, William A.; "The Control of Body Temperature In the Small Newborn Infant by Low Energy Infrared Radiation", 1963.
Sierracin Corporation, Medical Products Div. Brochure, "Sierracin Cradle Warmer Model IR-11".
"PPG Electrically Heated Transparency Systems for Aircraft-Marine Railroad", (date unknown but before this invention was reduced to practice).
"ElectriClear Heated Windshield Systems" by Libby Owens Ford, 1987.
J. J. Haggerty, "The Golden Canopies" from Spinoff 1978, a publication of the National Aeronautics and Space Administration, Jan. 1978.

Primary Examiner—Bruce A. Reynolds
Assistant Examiner—John A. Jeffery
Attorney, Agent, or Firm—Ratner & Prestia

[57] ABSTRACT

A radiant heater is provided, which can be in the form of an overlay on an existing incubator hood or integrated in an incubator hood. The heater has an optically transparent, radiotransparent and phototherapy transparent electrically conductive coating, preferably indium tin oxide.

35 Claims, 5 Drawing Sheets

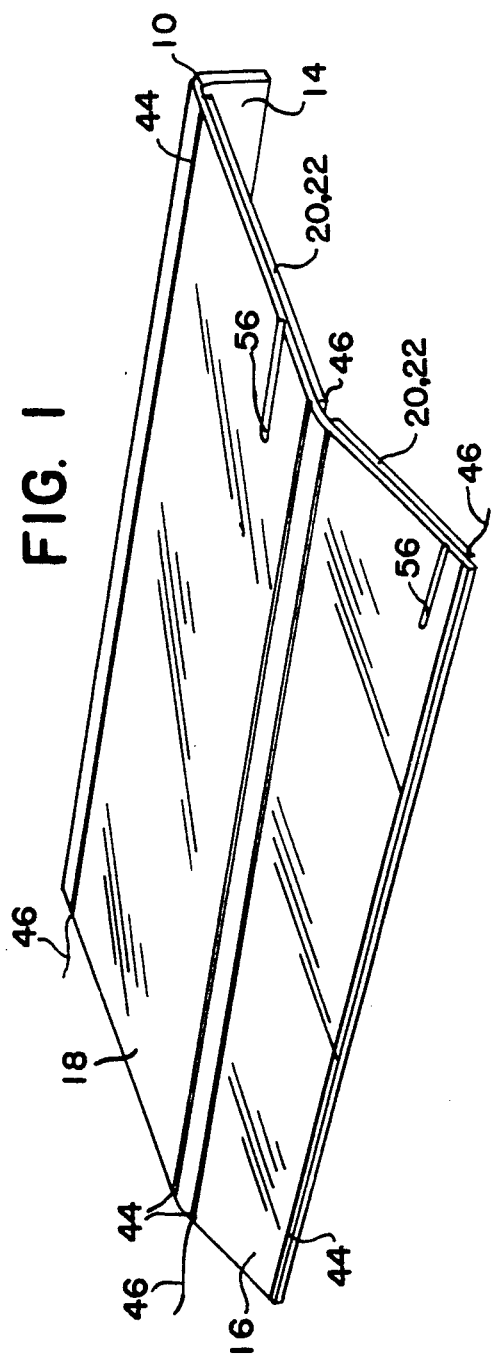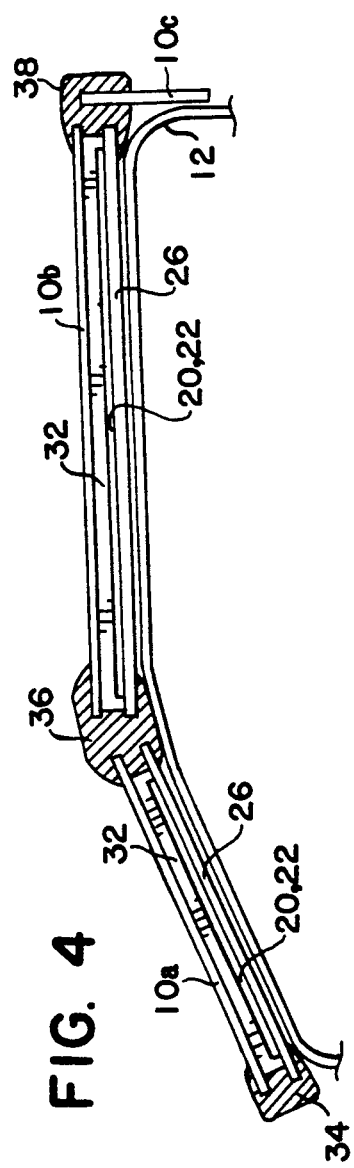

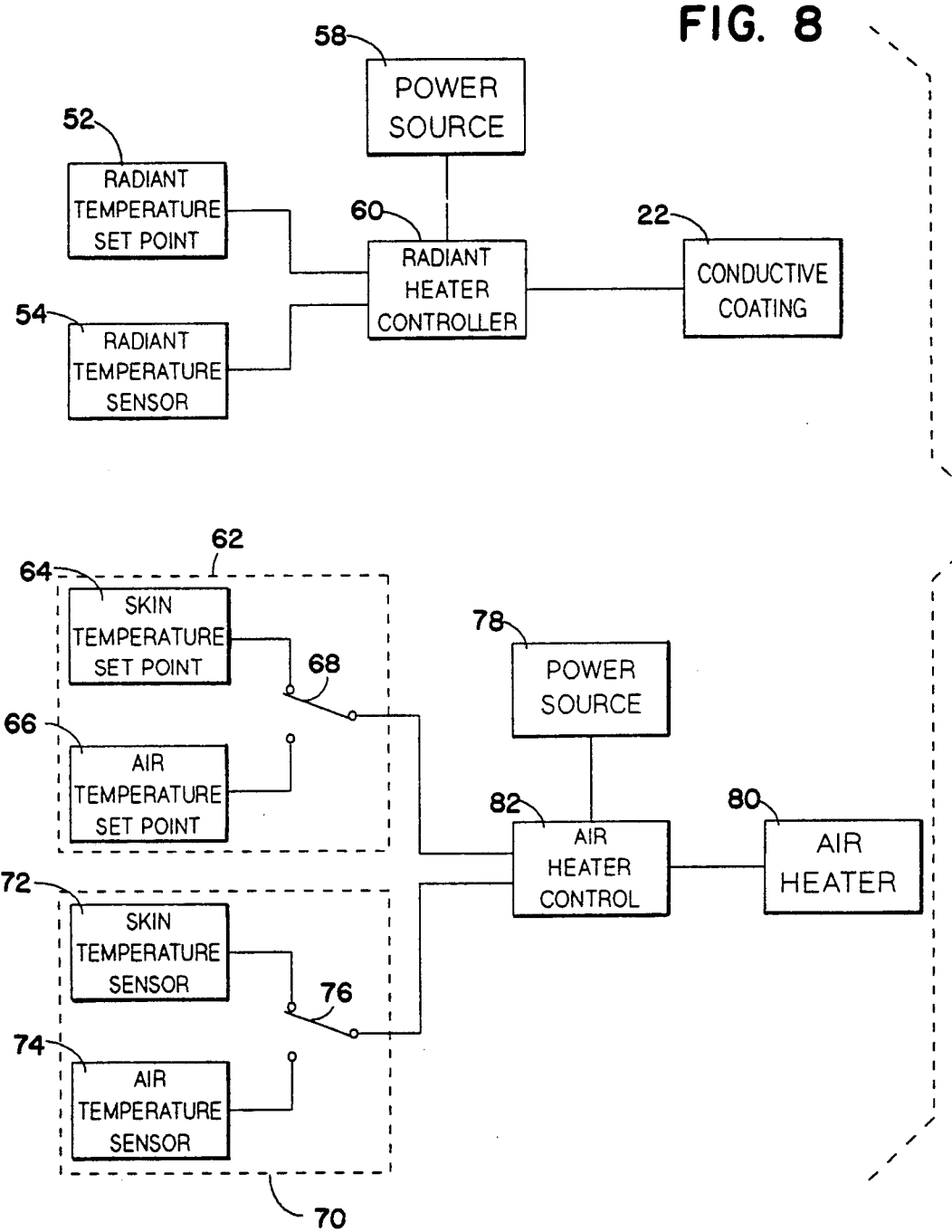

TRANSPARENT FILM RADIANT HEAT SOURCE FOR USE WITH INCUBATORS

BACKGROUND OF THE INVENTION

1. Field of the Invention

This invention relates, in general, to the treatment of infants and, more particularly, to optically transparent radiant heat sources for use with or incorporation into infant incubators to provide radiant heat to an infant being treated in an infant incubator.

2. Description of Related Art

Infant incubators are used in the treatment and maintenance of weak, sickly, premature or low birth weight infants in order to maintain infant body temperature and allow the infant to develop. Infants may lose heat in four ways: through evaporation, convection, conduction and radiation. Conductive heat loss in an infant is usually considered negligible, since the mattress upon which the infant is placed is generally an excellent insulator, and, therefore, such net heat loss is small. Evaporative heat loss is dependent upon the incubator air temperature and infant skin temperature differential, as well as the relative humidity of the incubator air and the air velocity across the infant's skin. Evaporative heat loss is often referred to as insensible water loss, and can be controlled by controlling the air flow characteristics of the incubator design, the incubator air temperature, and by adding humidity to the incubator air. Convective heat loss is also a function of the incubator air temperature and infant skin temperature differential. Radiative or radiant heat loss is a function of infant skin temperature and incubator wall temperature differential. Radiant heat loss is typically the major source of heat loss, except in the very first days in the life of a very premature, very low birth weight infant, when evaporative heat loss (insensible water loss) may be greater.

The amount of heat lost by any of the ways mentioned is dependent upon incubator design and the infant's metabolism. The desired objective of an incubator environmental control system is to provide a thermal environment which will place minimum demand on the infant's metabolism to maintain body temperature at its preferred level. Typically, this state of minimum metabolic demand is assumed to be achieved when an infant's skin temperature is maintained within a prescribed normal range.

Radiant heat loss from the infant may be reduced by minimizing radiant heat loss through the walls of the incubator. This is because the primary source of radiant heat loss in an incubator is cold incubator walls. Minimization of radiant heat loss through the incubator walls can be accomplished in either of two ways. First, by increasing the wall temperature of the incubator, the temperature differential between the infant and the incubator walls may be minimized. Second, by adding radiant energy directed to the infant through the walls of the incubator, the radiant heat lost by the infant may be balanced with the heat gained from the radiant source.

Hence, radiant warming has been used to add radiant energy to the infant. In some instances, incubators, such as the one shown in U.S. Pat. No. 3,858,570—Beld, et al., have been equipped with wires embedded in the hood of the incubator in order to radiate energy to the infant. Such arrangements have the disadvantage that the wires are opaque to X-rays, and interfere with visual inspection of the infant. Other incubators have been equipped with a plastic hood coated with an electrically conductive material, such as shown in U.S. Pat. No. 3,878,361—Levin et al. The coatings used have heretofore not been colorless. The coatings used generally have a yellow tint. This yellow tint causes difficulty in judging bilirubin levels in an infant making visual assessment of cyanosis more difficult.

SUMMARY OF THE INVENTION

In one preferred embodiment of the present invention, a radiant heat source is incorporated in an overlay for an incubator hood. This permits use of the present invention with incubators in service and provides flexibility in moving such an incubator overlay from one incubator to another. This overlay includes a rigid, transparent plastic sheet shaped to rest on an incubator hood and a film of transparent, plastic material having a transparent, electrically conductive coating on a surface thereof. This film, with the conductive coating, extends over a selected surface area of the rigid, transparent plastic sheet facing an incubator hood when the overlay rests on the incubator hood. Also included in this overlay is a set of conductor units which are electrically and mechanically connected to the transparent, electrically conductive coating. Each of these conductor units has a free end adapted for connection to an electric power source.

In another preferred embodiment of the present invention, the radiant heat source is incorporated in the hood of an incubator. The radiant heat source, when incorporated in the incubator hood, can be generally similar to the radiant heat source in the incubator hood overlay.

The electrically conductive coating, preferably indium tin oxide, is neutral in color and transparent to phototherapy wavelengths and to x-ray transmission. The radiant heat and resultant warm walls allow a high humidity level to be maintained in the incubator with greatly reduced condensation formation on the incubator walls and rainout from the incubator walls.

In one construction, applicable to both an incubator hood overlay and an incubator hood, the electrically conductive coating is bonded to the rigid transparent plastic sheet which is the main structural component of the overlay or incubator hood. In another construction, also applicable to both an incubator hood overlay and an incubator hood, the electrically conductive coating is bonded to a second rigid, transparent plastic sheet which serves as a layer of protective material and is spaced from the first rigid, transparent plastic sheet, so that an air gap is formed between the two plastic sheets. This acts as a double wall to aid heat retention for more efficient utilization of electrical energy and reduced surface temperature exposed to the operator.

In certain applications, it may be feasible to deposit the electrically conductive coating directly on the transparent plastic sheet and eliminate the use of the film of transparent, plastic material.

Yet another aspect of the present invention is the manner in which the temperature of the radiant heat source is maintained relative to the temperature of the air within the incubator hood. Electrical power is supplied to the electrically conductive coating of the radiant heat source to maintain the overlay or hood temperature at a preset level. Although this preset temperature level is selected with regard to the desired temperature of the air within the hood, the control of the overlay or hood temperature is independent of the control of the temperature of the air within the hood.

BRIEF DESCRIPTION OF THE FIGURES

FIG. 1 is a perspective view of a first embodiment of a radiant heat source constructed in accordance with the present invention in which the radiant heat source is incorporated in an overlay for an incubator hood.

FIG. 4 is a sectional view of a second embodiment of a radiant heat source constructed in accordance with the present invention in which the radiant heat source is incorporated in an overlay for an incubator hood.

FIG. 8 is a block diagram of the controls of an air heater in an incubator and a radiant heat source of the present invention.

DESCRIPTION OF THE PREFERRED EMBODIMENTS

Figure 2:
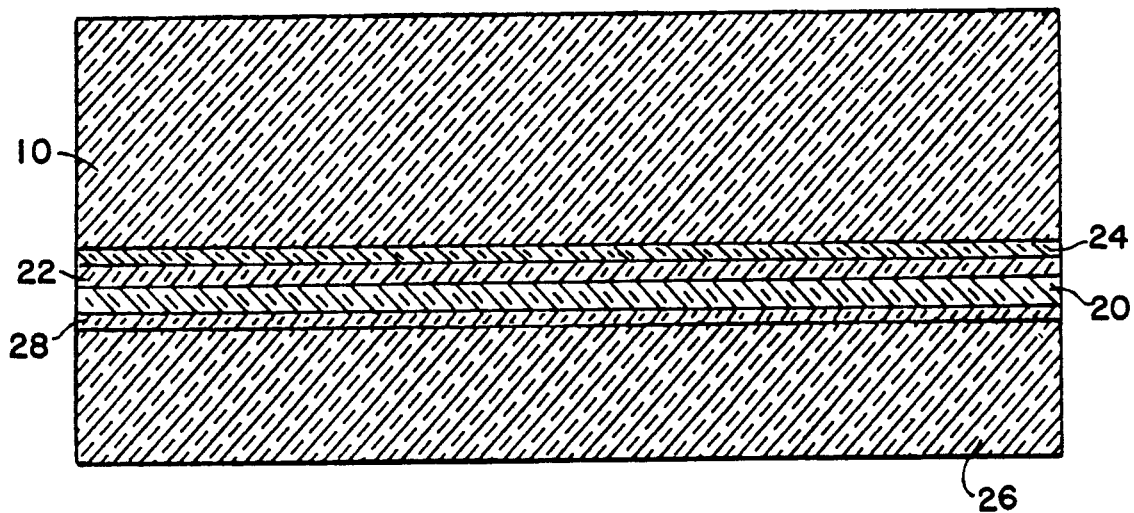
FIG. 2 is a partial cross-sectional view of a portion of a radiant heat source constructed in accordance with the present invention in which the protective layer is acrylic.
Figure 3:
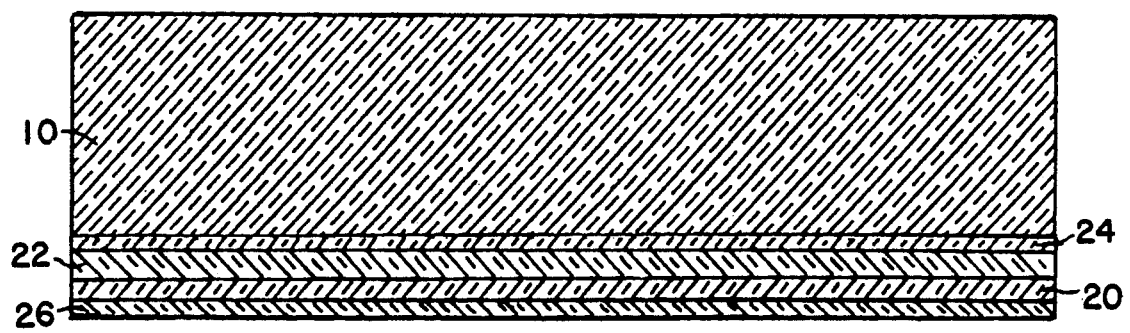
FIG. 3 is a partial cross-sectional view of a portion of a radiant heat source constructed in accordance with the present invention in which the protective layer is a self-adherent, abrasion resistant coating.

Referring to FIGS. 1 through 5, a radiant heat source overlay for an incubator hood, constructed in accordance with the present invention, includes a rigid, transparent plastic sheet 10 shaped to rest on an incubator hood. FIG. 4 shows one embodiment of such an overlay resting on an incubator hood 12. Plastic sheet 10 may be acrylic and, for the embodiment shown in FIG. 1, has a vertical portion 14 at its rear, an inclined portion 16 at its front and a horizontal portion 18 between vertical portion 14 and inclined portion 16. For other shaped incubator hoods, plastic sheet 10 is shaped accordingly.

As shown in FIG. 2, the radiant heat source overlay also includes a film 20 of transparent, plastic material having a transparent, electrically conductive coating 22 on a surface thereof. Film 20 may be a polyester, such as polyethylene terephthalate or other optically clear plastic. Electrically conductive coating 22 preferably is indium tin oxide which is optically clear and colorless and is transparent to X-rays and phototherapy.

Film 20, with conductive coating 22, extends over a selected surface area of plastic sheet 10 which faces an incubator hood when the overlay rests on the incubator hood. For the arrangement shown in FIG. 2, conductive coating 22 is between plastic sheet 10 and film 20 and is bonded to plastic sheet 10 by an adhesive layer 24 between plastic sheet 10 and conductive coating 22. For the radiant heat source overlay shown in FIG. 1, both inclined portion 16 and horizontal portion 18 can have a film 20 with a conductive coating 22.

Because film 20 and conductive coating 22 are somewhat delicate and can be scratched or marked, the overlay preferably further includes a layer 26 of protective material extending over the surface of film 20 opposite from the surface having conductive coating 22. For the embodiment of the invention shown in FIG. 2, protective layer 26 is a rigid, transparent plastic sheet to which film 20 is bonded by an adhesive layer 28, while for the embodiment of the invention shown in FIG. 3, protective layer 26 is a transparent layer of silicon dioxide which adheres well and, therefore, does not require an adhesive layer to be bonded to film 20. As with other components, the layer of protective material is optically clear and does not impede X-ray or phototherapy transmissions.

Figure 5:
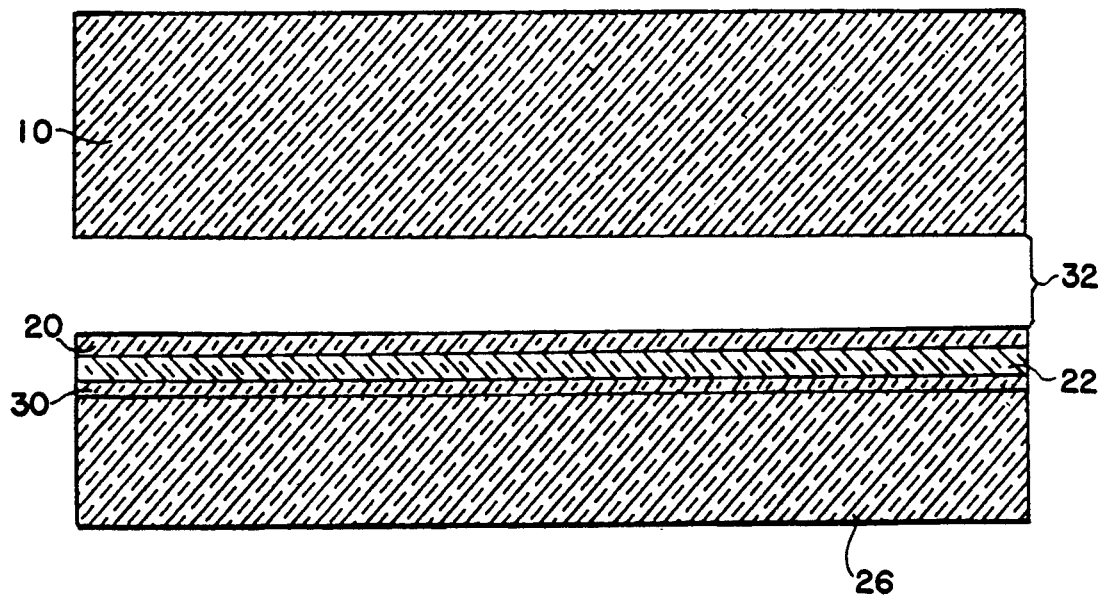
FIG. 5 is a partial cross-sectional view of a portion of a radiant heat source constructed in accordance with the present invention in which the protective layer is acrylic and spaced from the rigid plastic sheet.

In the embodiment of the invention shown in FIGS. 4 and 5, plastic sheet 10 has been replaced by three plastic sheets 10a, 10b and 10c and the overlay has been divided into three sections. Associated with at least one of plastic sheets 10a and 10b is a conductive coating 22 which is bonded to a protective layer 26, in the form of a rigid, transparent plastic sheet, by an adhesive layer 30 between protective layer 26 and conductive coating 22. Each plastic sheet, 10a, 10b, and 10c, along with the associated conductive coating 22, protective layer 26, adhesive layer 30 (if any), etc., combine to form one section of the overlay. As with the FIG. 1 embodiment of the invention, both the inclined portion 10a and the horizontal portion 10b of the FIG. 4 overlay can have a film 20 with a conductive coating 22. Protective layers 26 are so positioned, relative to plastic sheets 10a and 10b, that films 20 are spaced from plastic sheets 10a and 10b to provide air gaps 32, A preferably 0.080" to 0.100" wide, which act as a dead air space and thermal barrier. A plurality of longitudinal ribs 34, 36 and 38 serve to space protective layers 26 from plastic sheets 10a and 10b and to hold the sections together to form an overlay. Gaps 32 are sealed by suitable means along longitudinal ribs 34, 36 and 38 and at their respective ends after evacuation of the air. The overlay of FIGS. 4 and 5 thus acts as an insulator, in the same way as a double wall incubator. The thermal barrier provided by gaps 32 prevents heat from being carried away from protective layers 26 by conduction. Further, since the spaces between sheets 10a and 26 and between sheets 10b and 26 are sealed, films 20 and conductive coatings 22 are well protected.

It should be understood that a single wall version of the present invention, whether the radiant heat source is incorporated in an overlay or in an incubator hood, also can be formed from two or more sections. For example, in FIG. 1, vertical portion 14, inclined portion 16, and horizontal portion 18 can be separate pieces held together by suitable means.

Figure 6:
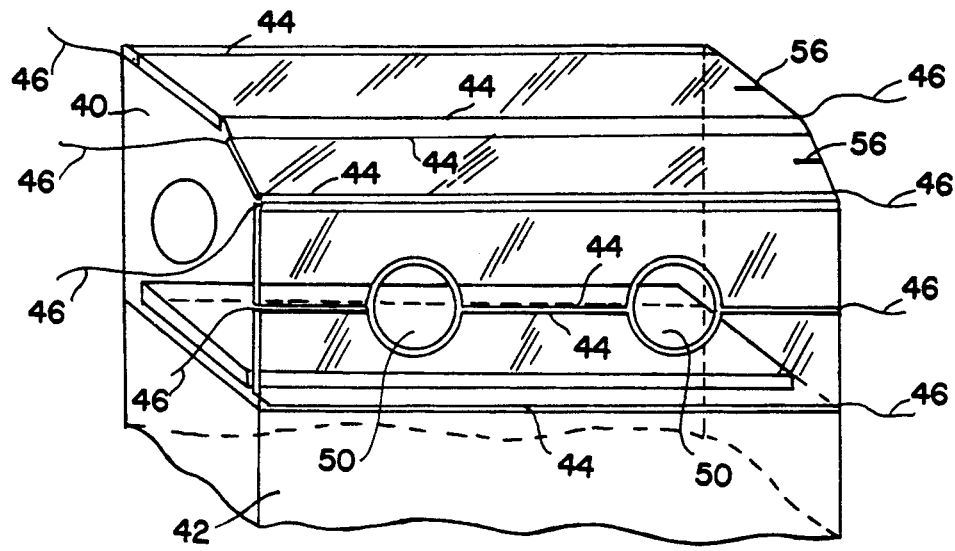
FIG. 6 is a perspective view of a third embodiment of a radiant heat source constructed in accordance with the present invention in which the radiant heat source is incorporated in the hood of an incubator.

As indicated above, a radiant heat source, constructed in accordance with the present invention, can be incorporated directly into an incubator hood. FIG. 6 shows a portion of an incubator having a hood 40 mounted on a base 42. For additional information about the construction and operation of an incubator, U.S. Pat. No. 3,335,713 is incorporated herein by reference. Hood 40 of FIG. 6 is shaped generally similar to the overlays shown in FIGS. 1 and 4, so that the descriptions of the overlays previously given apply to the radiant heat source of the present invention when it is incorporated in an incubator hood. In particular, film 20, with conductive coating 22, can be applied to the inside, concave surface of the incubator hood and provided with a suitable protective layer or it can be applied to a protective layer spaced from the concave surface of the hood, thereby forming a double wall hood. Also, film 20, with conductive coating 22, can be applied to selected inner surfaces of hood 40 in the same manner as with the overlays of FIGS. 1 and 4.

Figure 7:
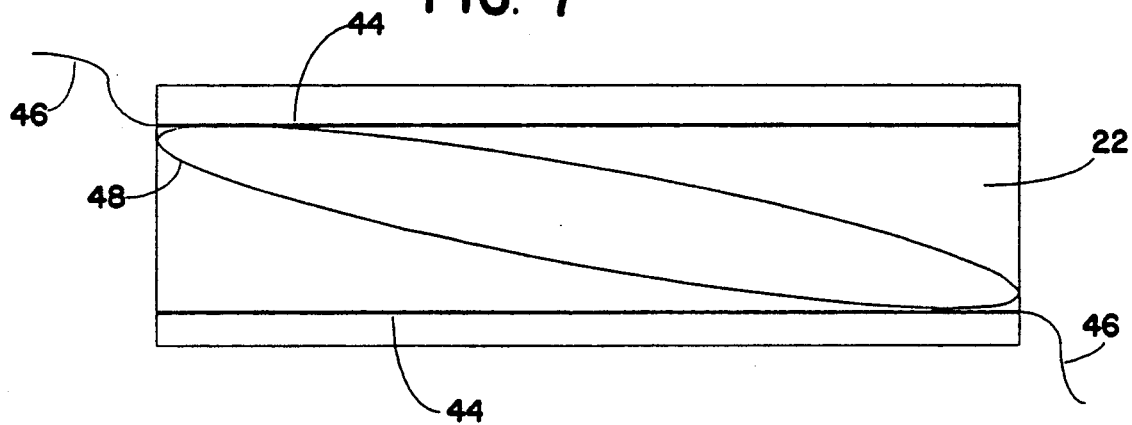
FIG. 7 is a plan view of one section of a radiant heat source constructed in accordance with the present invention.

FIG. 7 is a plan view of one portion of an overlay or incubator hood having a radiant heat source according to the present invention. As shown by FIG. 7, each such portion has a set of conductor units with each conductor unit composed of a bus bar 44 and a lead wire 46. Each bus bar 44 extends along an edge of conductive coating 22 and is electrically and mechanically attached to the conductive coating. Each lead wire 46 extends from an end of a bus bar and has a free end adapted for connection to an electrical power source. Bus bars 44 are high conductivity/low resistance elements which deliver power to conductive coating 22. Lead wires 46 are preferably attached at opposite ends, and most preferably at opposite corners, of a rectangular shaped conductive coating 22 such as the one illustrated in FIG. 7. Due to power losses along the lengths of bus bars 44 and conductive coating 22, maximum radiation occurs along a line between the connections of lead wires 46 to bus bars 44. Radiation output decreases as one moves farther from this line. Hence, curves of constant radiation output occur. One such constant radiation output curve is identified by reference numeral 48 in FIG. 7. Radiation output outside of this curve is lower than radiation output inside the curve. This radiation gradient is minimized by locating lead wires 46 at opposite corners of the rectangular conductive coating because this configuration produces a longer and larger curve 48 and thus a more uniform pattern of radiation than what would be produced by locating both lead wires at one end of the rectangle.

As indicated above, a radiant heat source, according to the present invention, can be arranged as a plurality of smaller radiant heat sources rather than a single, larger radiant heat source. Among the reasons for multiple radiant heat sources is that manufacturing constraints make it easier to produce a multi-part radiant heater than one large radiant heater, especially when the overlay or incubator hood is arranged as a double wall unit. Also, safety and control considerations may dictate the use of a multi-part radiant heater.

In manufacturing a single wall overlay or hood according to the present invention, the polyester film 20 is first coated with an indium tin oxide coating 22 by a standard coating process used for this material. The coated film is then bonded to a flat sheet of acrylic 10. The acrylic sheet is then heated and bent to form either an overlay structure or an incubator hood structure.

The acrylic sheet is heated only where the bends are to be made. If the entire sheet were covered with one radiant heater, the areas needed to be heated to bend the acrylic sheet would necessarily include areas covered by the radiant heater. When such areas are heated, the adhesive bonding the radiant heater to the acrylic sheet tends to outgas and bubble up. This can adversely affect the radiant, optical, and conductive properties of the conductive coating. Therefore, those areas of the acrylic sheet to be bent are not covered by the radiant heater component.

Alternatively, the radiant heater can be applied after the acrylic sheet has been bent into the overlay or hood shape. The radiant heater preferably would still be divided into separate, smaller units because film 20 is difficult to apply evenly over bends. Further, other considerations to be discussed presently generally dictate that smaller radiant heaters are preferred over one large radiant heater.

The disposition of conductive coating 22 is determined, primarily, by the assembly of the radiant heat source of the invention. In order to provide both physical protection and protection against chemical attack to the conductive coating as soon as possible, it is the conductive coating which is bonded to the top transparent sheet or to the lower transparent sheet in the double wall embodiments. This indicates that the conductive coating can be between the transparent film and the infant within the hood or that the transparent film can be between the conductive coating and the infant.

Conductive coating 22 can be applied directly to acrylic sheet 10, but the process is costly. The direct application produces acceptable results, but due to cost, the previously described method, namely applying electrically conductive coating 22 to polyester film 20 and then bonding the coated film to the acrylic sheet is preferred. If the conductive coating is applied directly to the acrylic sheet, adhesive layer 24 and polyester film 20 may be eliminated.

The second reason for arranging the radiant heat source in two or more parts is that the resistance between the bus bars, and, therefore, the voltage needed to energize a radiant heater, varies directly with the distance between the bus bars. Therefore, as the radiant heater becomes larger, the voltage which is required becomes greater. General safety considerations make it desirable that the voltage remain as low as possible, and, therefore, it is desirable to use separate, smaller radiant heaters instead of one large radiant heater.

Also, by using smaller, separate radiant heaters, each one, having separate conductor units, may be separately controlled. In addition, arranging the radiant heat source as smaller, separate radiant heaters allows filling the areas around the access ports (arm holes) 50, which are incorporated into the hood to allow access to the infant without removing the hood.

FIG. 8 is a block diagram which shows how the temperature within the hood of an incubator can be controlled whether a radiant heat source, constructed in accordance with the present invention, is incorporated in an overlay adapted to rest on the incubator hood or in the hood itself. To control the radiant heat source, the control system includes means 52 for supplying a first signal representative of the desired temperature of transparent sheet 10. Such means may include a conventional temperature setting circuit composed of a ladder network or a potentiometer arrangement. The control system also include means 54 for sensing the temperature of transparent sheet 10 and for supplying a second signal representative of the temperature of transparent sheet 10. Such means may include a thermometer of conventional construction and operation and identified by reference numeral 56 in FIGS. 1 and 6. When the radiant heat source is incorporated in a double wall arrangement, the temperature sensor may be placed in the gap between the two walls but in contact with the outer transparent sheet.

The control system further includes a first power source 58 which supplies electrical power to conductive coating 22 which, in turn, heats transparent sheet 10. Power source 58 may be a conventional incubator power supply.

The amount of power supplied by power source 58 to conductive coating 22 is controlled by means 60 which are responsive to the first signal, representative of the desired transparent sheet temperature, and the second signal, representative of the actual transparent sheet temperature. Means 82 typically include a differential amplifier arrangement which develops an output representative of the difference between the desired temperature and the actual temperature and this output is used to regulate the amount of power needed to heat the transparent sheet to the desired temperature.

The control system of FIG. 8 also controls the temperature of the air circulated into the hood from the base. The arrangement shown in FIG. 8 for serving this function is fairly standard for commercially available incubators and includes means 62 for supplying a third signal representative of the desired temperature of either the skin of an infant within the hood or the air within the hood. Such means may include conventional temperature setting circuits composed of a ladder network or a potentiometer arrangement with one, identified by reference numeral 64, setting skin temperature and the other, represented by reference numeral 66, setting the air temperature. A switch 68 serves to select one of these two settings upon which control of the air temperature is based.

Also included in the control system are means 70 for sensing the actual temperature of the skin of an infant within the hood and the actual temperature of the air within the hood and for supplying a fourth signal representative of either the actual skin temperature or the actual air temperature. Such means may include a conventional skin temperature probe, represented by reference numeral 72, a conventional thermometer, represented by reference numeral 74, and a switch 76 for selecting between the outputs from the skin temperature probe and the thermometer.

The control system further includes a second power source 78 which supplies electrical power to an air heater 80, typically located in the base of the incubator. Power source 78 may be a conventional incubator power supply. Air heater 80 also may be of conventional construction and operation.

The amount of power supplied by power source 78 to air heater 80 is controlled by means 82 which are responsive to the third signal, representative of the desired skin temperature or the desired air temperature and the fourth signal, representative of the actual skin temperature or the actual air temperature. Means 82 typically include a differential amplifier arrangement which develops an output representative of the difference between the desired temperature of the selected parameter and the actual temperature of the selected parameter and this output is used to regulate the amount of power needed to heat the air to the desired air temperature or to a level sufficient to develop the desired skin temperature.

Although the radiant heat source and the air heater are separately controlled, the settings of the control parameters for each of the two should be considered together. For example, the radiant heater set point should not be so great that the heat radiated from the radiant heater adversely affects the infant. It should be remembered that, for the arrangement of the control system shown in FIG. 8, the radiant heater is not controlled by either the infant's skin temperature or the temperature of the air with in the hood, so that setting the radiant heater temperature too high can affect the infant adversely because the monitored parameter has no effect of the power supplied to the radiant heater.

EXPERIMENTAL RESULTS

Two sets of tests were performed to determine the effectiveness of the radiant heating overlay in aiding heat retention in an Isolette [Isolette is a registered trademark of Air-Shields, Inc.] Model C100 single wall incubator. The results were compared against control experiments using Isolette single and double wall incubators without radiant heaters.

The first set of tests was performed with an ambient temperature of 20° C. This temperature was selected because it is reasonably extreme and would aid in producing quantifiable, comprehensible results. Further, the ambient incubator temperature differentials were such that efficacy of the radiant heater as a determinant in reducing condensation due to high incubator humidity could be observed. Each incubator was set for an internal air temperature of 37° C. Case A was the single wall incubator; Case B was the double wall incubator; and Case C was the single wall incubator with the radiant heater overlay.

In each incubator was placed a SAM VI simulator in which the surface and core temperatures were measured. Air temperature at mattress level was measured at five points around the mattress. The mattress was tilted during the tests to discover the effect of radiant heating during Fowler and Trendelenberg positions (the Fowler position is with the infant's head raised above the feet, Trendelenberg position is feet raised above the head). The results of these tests are shown in Table 1.

TABLE 1

|  | Case A Single Wall | Case B Double Wall | Case C Single wall With Heater |
|---|---|---|---|
| Mattress Level |  |  |  |
| Center Mattress | 37.1° C. | 36.7° C. | 37.2° C. |
| Uniformity | 0.4° C. | 0.3° C. | 0.2° C. |
| SAM VI Skin | 34.9° C. | 36.1° C. | 37.4° C. |
| SAM VI Core | 34.7° C. | 35.6° C. | 37.3° C. |
| Mattress Tilted Fowler |  |  |  |
| Center Mattress | 36.6° C. | 36.2° C. | 37.6° C. |
| Uniformity | 0.4° C. | 1.4° C. | 0.2° C. |
| SAM VI Skin | 34.7° C. | 35.3° C. | 37.7° C. |
| SAM VI Core | 34.7° C. | 35.7° C. | 37.5° C. |
| Trendelenberg |  |  |  |
| Center Mattress | 35.3° C. | 34.1° C. | 37.3° C. |
| Uniformity | 0.6° C. | 1.1° C. | 0.3° C. |
| SAM VI Skin | 34.4° C. | 35.1° C. | 37.7° C. |
| SAM VI Core | 34.2° C. | 35.2° C. | 37.7° C. |
| Humidity Observations |  |  |  |
| 80% Relative Humidity | Heavy condensation & heavy rainout over most internal areas | Condensation in corners, right side, & upper hood rainout near corners | Condensation in corners, light condensation in main access panel |
| Test Conditions | Set Point - 37° C. Ambient Temperature - 20.1° C. average Test Unit - Isolette C100 incubator Hood Heater (case C) - overlay with 3 separate heaters @ 100 ohms/in$^2$ at surface temp set point of 46.5° C. SAM VI - simulator with a surface-to-mass ratio equivalent to a 1 kilogram infant | | |

The tests revealed that mattress temperature uniformity was much better in the incubator with the radiant heater overlay than in those incubators without the heater, with the mattress flat, uniformity in Case C was 0.2° C. as compared to 0.3° C. for Case B and 0.4° C. in Case A. A desirable value for mattress uniformity is considered to be 0.5° C., which all three incubators met with the mattress flat. In the Trendelenberg position, mattress uniformity was 0.6° C., 1.1° C., and 0.3° C. for Cases A, B, and C respectively. In the Fowler position, the mattress uniformity was 0.4° C., 1.4° C., and 0.2° C. for Cases A, B, and C respectively. Thus, only the incubator equipped with the radiant heater (Case C) performed satisfactorily in the Trendelenberg position test, and Case C clearly out-performed the other incubators in both the Fowler position test and in the test with the mattress flat.

The SAM VI skin and core temperatures did not reach the set temperatures of 37° C. in Cases A and B during the 19 hour test duration. In Case C, SAM VI skin temperature reached 37° C. in approximately 5 hours. SAM VI core temperature reached 37° C. in 6 hours, 24 minutes. After reaching set temperatures, the SAM VI skin and core temperatures fluctuated above and below set temperatures, indicating that thermal equilibrium had been reached.

With 80% relative humidity, Case A (single walled incubator) showed heavy condensation and heavy rainout over most internal areas. Case B (double walled incubator) showed condensation in the corners and on the upper hood, and rainout near the corners of the hood. Case C (single walled incubator including the radiant heater overlay of the present invention) showed noticeable condensation in the corners of the hood and light condensation in the main access panel, but no rainout occurred in the incubator. Thus Case C was highly acceptable.

The conditions of the second set of tests were identical to those of the first set, except that the ambient air temperature was 31° C. The results of those tests are summarized in Table 2 and need not be set out here. Summarily, those results showed trends similar to those shown by the first set of tests, though the magnitude of the differences among incubators was smaller since the test conditions were less severe. Thus, the incubator with the radiant heater overlay consistently out performed those without the overlay.

TABLE 2

|  | Case D Single Wall | Case E Double Wall | Case F Single wall With Heater |
|---|---|---|---|
| Mattress Level |  |  |  |
| Center Mattress | 36.4° C. | 36.4° C. | 37.0° C. |
| Uniformity | 0.3° C. | 0.3° C. | 0.1° C. |
| SAM VI Skin | 35.5° C. | 36.1° C. | 37.5° C. |
| SAM VI Core | 35.2° C. | 35.9° C. | 37.1° C. |
| Mattress Tilted Fowler |  |  |  |
| Center Mattress | 35.5° C. | 36.0° C. | 37.1° C. |
| Uniformity | 1.1° C. | 0.8° C. | 0.6° C. |
| SAM VI Skin | 34.8° C. |  | 38.1° C. |
| SAM VI Core | 35.1° C. |  | 37.8° C. |
| Trendelenberg |  |  |  |
| Center Mattress | 35.4° C. | 35.3° C. | 37.2° C. |
| Uniformity | 0.4° C. | 0.4° C. | 0.6° C. |
| SAM VI Skin | 35.0° C. |  | 38.1° C. |
| SAM VI Core | 35.0° C. |  | 38.0° C. |
| Humidity Observations |  |  |  |
| 80% Relative Humidity | Condensation, rainout, vision obscured in area around front panel | Condensation at sides and front panel | No condensation observed |
| Test | Set Point - 37° C. |  |  |

TABLE 2-continued

|  | Case D Single Wall | Case E Double Wall | Case F Single wall With Heater |
|---|---|---|---|
| Conditions | Ambient Temperature - 31° C. average Test Unit - Isolette C100 incubator Hood Heater (case F) - overlay with 3 separate heaters @ 100 ohms/in$^2$ at surface temp set point of 52° C. SAM VI - simulator with a surface-to-mass ratio equivalent to a one kilogram infant |  |  |

It is understood that various other modifications will be apparent to and can be readily made by those skilled in the art without departing from the spirit and scope of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A radiant heat source overlay for an incubator hood comprising:
   a rigid, transparent plastic sheet shaped to rest on an incubator hood and adapted to be removably placed on said hood;
   a film of transparent, plastic material having a transparent, electrically conductive coating on a surface thereof and extending over a selected surface area of said rigid, transparent plastic sheet facing an incubator hood when said overlay rests on said incubator hood; and
   a set of incubator units electrically and mechanically connected to said transparent, electrically conductive coating with each of said conductor units having a free end adapted for connection to an electrical power source.

2. A radiant heat source overlay according to claim 1 wherein said transparent, electrically conductive coating is between said rigid, transparent plastic sheet and said film of transparent, plastic material.

3. A radiant heat source overlay according to claim 2 further including a layer of protective material extending over the surface of said film of transparent, plastic material opposite from said surface having said transparent, electrically conductive coating.

4. A radiant heat source overlay according to claim 3 wherein said transparent, electrically conductive coating is bonded to said rigid, transparent plastic sheet by an adhesive layer between said rigid, transparent plastic sheet and said transparent, electrically conductive coating.

5. A radiant heat source overlay according to claim 1 wherein said film of transparent, plastic material is between said rigid, transparent plastic sheet and said transparent, electrically conductive coating.

6. A radiant heat source overlay according to claim 5 further including a layer of protective material extending over said transparent, electrically conductive coating.

7. A radiant heat source overlay according to claim 6 wherein said transparent, electrically conductive coating is bonded to said layer of protective material by an adhesive layer between said layer of protective material and said transparent, electrically conductive coating.

8. A radiant heat source overlay according to claim 4 wherein said layer of protective material is a rigid, transparent plastic sheet.

9. A radiant heat source overlay according to claim 4 wherein said layer of protective material is a transparent layer of silicon dioxide.

10. A radiant heat source overlay according to claim 4 wherein said transparent, electrically conductive coating is indium tin oxide.

11. A radiant heat source overlay according to claim 7 wherein said layer of protective material is a rigid, transparent plastic sheet.

12. A radiant heat source overlay according to claim 7 wherein said transparent, electrically conductive coating is indium tin oxide.

13. An incubator comprising:
a base;
a hood mounted on said base; and
a radiant heat source overlay resting on said hood, adapted to be removably placed on said hood, and having;
  (a) a rigid, transparent plastic sheet shaped to rest on an incubator hood;
  (b) a film of transparent, plastic material having a transparent, electrically conductive coating on a surface thereof and extending over a selected surface area of said rigid, transparent plastic sheet facing an incubator hood when said overlay rests on said incubator hood; and
  (c) a set of conductor units electrically and mechanically connected to said transparent, electrically conductive coating with each of said conductor units having a free end adapted for connection to an electrical power source.

14. An incubator according to claim 13 further including:
  (a) means for supplying a first signal representative of a desired temperature of said transparent plastic sheet;
  (b) means for sensing the temperature of said transparent plastic sheet and for supplying a second signal representative of said temperature of said transparent plastic sheet;
  (c) a first power source;
  (d) means responsive to said first and said second signals for supplying power from said first power source to said transparent, electrically conductive coating to heat said transparent plastic sheet to said desired temperature;
  (e) means for supplying a third signal representative of the desired temperature of one of the skin temperature of an infant within said hood and the air temperature within said hood;
  (f) means for sensing one of said skin temperature of an infant within said hood and said air temperature within said hood and for supplying a fourth signal representative of one of said skin temperature of an infant within said hood and said air temperature within said hood;
  (g) a second power source;
  (h) an air heater; and
  (i) means responsive to said third and said fourth signals for supplying power from said second power source to said air heater to heat said air within said hood to one of said desired air temperature within said hood and a level sufficient to develop said desired skin temperature of an infant within said hood.

15. An incubator according to claim 13 further including:
  (a) a first power source;
  (b) means for controlling power supplied from said first power source to said transparent, electrically conductive coating to heat said transparent plastic sheet;
  (c) a second power source;
  (d) an air heater; and
  (e) means for controlling power supplied from said second power source to said air heater to heat air within said hood.

16. A radiant heat source overlay for an incubator hood comprising:
a vertical section;
an inclined section;
a horizontal section between said vertical section and said inclined section;
said inclined and horizontal sections each including:
  (a) a first rigid transparent plastic sheet;
  (b) a second rigid transparent plastic sheet;
  (c) a film of transparent, plastic material having a transparent, electrically conductive coating on a surface thereof, said film disposed between said first and second sheets; and
  (d) a set of conductor units electrically and mechanically connected to said electrically conductive coating with each of said conductor units having a free end adapted for connection to an electrical power source; and
means for holding said sections in a fixed relationship to one another.

17. A radiant heat source according to claim 16 wherein each said electrically conductive coating is bonded to one of its respective rigid transparent sheets, and said respective first and second rigid transparent sheets are spaced apart, forming an air gap between each said transparent plastic film and the other respective rigid transparent sheet of said section.

18. A radiant heat source according to claim 17, wherein said electrically conductive coating is indium tin oxide.

19. A radiant heat source overlay for an incubator hood comprising:
a rigid, transparent plastic sheet shaped to rest on an incubator hood and adapted to be removably placed on said hood;
an electrically conductive coating on a selected surface area of said rigid, transparent plastic sheet facing an incubator hood when said overlay rests on said incubator hood; and
a set of conductor units electrically and mechanically connected to said transparent, electrically conductive coating with each of said conductor units having a free end adapted for connection to an electrical power source.

20. A radiant heat source overlay for an incubator hood comprising:
a rigid, transparent plastic sheet shaped to rest on an incubator hood;
a film of transparent, plastic material having a transparent, electrically conductive coating on a surface thereof and extending over but spaced from a selected surface area of said rigid, transparent plastic sheet facing an incubator hood when said overlay rests on said incubator hood, said film situated between said, rigid, transparent plastic sheet and said transparent, electrically conductive coating;

a rigid, transparent plastic sheet of protective material extending over said transparent, electrically conductive coating and bonded to said transparent, electrically conductive coating by an adhesive layer between said sheet of protective material and said transparent, electrically conductive coating; and a set of conductor units electrically and mechanically connected to said transparent, electrically conductive coating with each of said conductor units having a free end adapted for connection to an electrical power source.

21. A radiant heat source overlay according to claim 20 wherein said transparent, electrically conductive coating is indium tin oxide.

22. A radiant heat source overlay for an incubator hood comprising:

a rigid, transparent plastic sheet shaped to rest on an incubator hood, and having:
  (a) a vertical portion,
  (b) an inclined portion, and
  (c) a horizontal portion between said vertical portion and said inclined portion;

a film of transparent, plastic material having a transparent, electrically conductive coating on a surface thereof, between said film and said horizontal portion of said rigid, transparent plastic sheet and said transparent, electrically conductive coating, said coating extending over a selected surface area of said horizontal portion of said rigid, transparent sheet facing an incubator hood when said overlay rests on said incubator hood;

a layer of protective material extending over the surface of said film of transparent, plastic material opposite from said surface having said transparent, electrically conductive coating;

a set of conductor units electrically and mechanically connected to said transparent, electrically conductive coating with each of said conductor units having a free end adapted for connection to an electrical power source;

a second film of transparent, plastic material having a transparent, electrically conductive coating on a surface thereof bonded by an adhesive layer to a surface of said inclined portion of said rigid, transparent plastic sheet facing said incubator hood;

a second set of conductor units electrically and mechanically connected to said transparent, electrically conductive coating of said second film of transparent, plastic material; and a second layer of protective material extending over the surface of said second film of transparent, plastic material opposite from said surface having said transparent, electrically conductive coating.

23. A radiant heat source overlay according to claim 22 wherein each of said conductor units includes a bus bar extending along an edge of a transparent, electrically conductive coating and a lead wire extending from an end of said bus bar and said bus bars of a set of conductor units extend along opposite edges of their associated transparent, electrically conductive coating.

24. A radiant heat source overlay according to claim 23 wherein said lead wires of one set of conductor units extend from their associated bus bars at opposite ends of their associated transparent, electrically conductive coating.

25. A radiant heat source overlay for an incubator hood comprising:

a rigid, transparent plastic sheet shaped to rest on an incubator hood, and having:
  (a) a vertical portion,
  (b) an inclined portion, and
  (c) a horizontal portion between said vertical portion and said inclined portion;

a film of transparent, plastic material having a transparent, electrically conductive coating on a surface thereof and extending over said horizontal portion of said rigid, transparent plastic sheet and facing an incubator hood when said overlay rests on said incubator hood, said film situated between said horizontal portion of said rigid transparent plastic sheet and said transparent electrically conductive coating;

a layer of protective material extending over said transparent, electrically conductive coating and to which said transparent, electrically coating is bonded by an adhesive layer between said layer of protective material and said transparent, electrically conductive coating;

a set of conductor units electrically and mechanically connected to said transparent, electrically conductive coating with each of said conductor units having a free end adapted for connection to an electrical power source;

a second film of transparent, plastic material having a transparent, electrically conductive coating on a surface thereof and extending over a surface of said inclined portion of said rigid, transparent plastic sheet facing an incubator hood when said overlay rests on said incubator hood;

a second set of conductor units electrically and mechanically connected to said transparent, electrically conductive coating of said second film of transparent, plastic material; and a second layer of protective material to which said transparent, electrically conductive coating of said second film of transparent material is bonded by an adhesive layer between said second layer of protective material and said transparent, electrically conductive coating of said second film of transparent material.

26. A radiant heat source overlay according to claim 25 wherein each of said conductor units includes a bus bar extending along an edge of a transparent, electrically conductive coating and a lead wire extending from an end of said bus bar and said bus bars of a set of conductive units extend along opposite edges of their associated transparent, electrically conductive coating.

27. A radiant heat source overlay according to claim 26 wherein said lead wires of one set of conductor units extend from their associated bus bars at opposite ends of their associated transparent, electrically conductive coating.

28. An incubator hood having a radiant heat source comprising:

a rigid, transparent plastic sheet formed into a concave structure and having:
  (a) a vertical portion,
  (b) an inclined portion, and
  (c) a horizontal portion between said vertical portion and said inclined portion;

a film of transparent, plastic material having an indium tin oxide coating on a surface thereof between said film and said horizontal portion of said rigid, transparent plastic sheet and bonded to an inside surface of said horizontal portion of said rigid, transparent plastic sheet by an adhesive layer between said horizontal portion of said rid, transparent plastic sheet and said indium tin oxide coating;

a layer of protective material extending over the surface of said film of transparent, plastic material opposite from said surface having said indium tin oxide coating;

a set of conductor units electrically and mechanically connected to said indium tin oxide coating with each of said conductor units having a free end adapted for connection to an electrical power source;

a second film of transparent, plastic material having an indium tin oxide coating on a surface thereof bonded by an adhesive layer to a surface of said inclined portion of said rigid, transparent plastic sheet facing said incubator hood;

a second set of conductor units electrically and mechanically connected to said indium tin oxide coating of said second film of transparent, plastic material; and a second layer of protective material extending over the surface of said second film of transparent, plastic material opposite from said surface having said indium tin oxide coating.

29. An incubator hood according to claim 28 wherein each of said conductor units includes a bus bar extending along an edge of an indium tin oxide coating and a lead wire extending from an end of said bus bar and said bus bars of a set of conductive units extend along opposite edges of their associated indium tin oxide coating.

30. An incubator hood according to claim 29 wherein said lead wires of one set of conductive units extend from their associated bus bars at opposite ends of their associated indium tin oxide coating.

31. An incubator hood having a radiant heat source comprising:

a rigid, transparent plastic sheet formed into a concave structure and having:
(a) a vertical portion,
(b) an inclined portion, and
(c) a horizontal portion between said vertical portion and said inclined portion;

a film of transparent, plastic material having an indium tin oxide coating on a surface thereof and extending over an inside surface of said horizontal portion of said rigid, transparent plastic sheet, said film situated between said horizontal portion of said rigid, transparent plastic sheet and said indium tin oxide coating;

a layer of protective material extending over said indium tin oxide coating and to which said indium tin oxide is bonded by an adhesive layer between said layer of protective material and said indium tin oxide coating;

a set of conductor units electrically and mechanically connected to said indium tin oxide coating with each of said conductor units having a free end adapted for connection to an electrical power source;

a second film of transparent, plastic material having an indium tin oxide coating on a surface thereof and extending over a surface of said inclined portion of said rigid, transparent plastic sheet facing said incubator hood;

a second set of conductor units electrically and mechanically connected to said indium tin oxide coating of said second film of transparent, plastic material; and a second layer of protective material to which said indium tin oxide coating of said second film of transparent material is bonded by an adhesive layer between said second layer of protective material and said indium tin oxide coating of said second film of transparent material.

32. An incubator hood according to claim 31 wherein each of said conductor units includes a bus bar extending along an edge of an indium tin oxide coating and a lead wire extending from an end of said bus bar and said bus bars of a set of conductor units extend along opposite edges of their associated indium tin oxide coating.

33. An incubator hood according to claim 32 wherein said lead wires of one set of conductor units extend from their associated bus bars at opposite ends of their associated indium tin oxide coating.

34. An incubator hood having a radiant heat source comprising:

a rigid, transparent plastic sheet formed into a concave structure and having:
(a) a vertical portion,
(b) an inclined portion, and
(c) a horizontal portion between said vertical portion and said inclined portion;

a film of transparent, plastic material having a transparent, electrically conductive coating on a surface thereof between said film and a first of said portions of said rigid, transparent plastic sheet and bonded to an inside surface of said first of said portions of said rigid, transparent plastic sheet by an adhesive layer between said first of said portions of said rigid, transparent plastic sheet and said transparent, electrically conductive coating;

a layer of protective material extending over the surface of said film of transparent, plastic material opposite from said surface having said transparent, electrically conductive coating;

a set of conductor units electrically and mechanically connected to said transparent, electrically conductive coating with each of said conductor units having a free end adapted for connection to an electrical power source;

a second film of transparent, plastic material having a transparent, electrically conductive coating on a surface thereof bonded by an adhesive layer to a surface of a second of said portions of said rigid, transparent plastic sheet facing said incubator hood;

a second set of conductor units electrically and mechanically connected to said transparent, electrically conductive coating of said second film of transparent, plastic material; and a second layer of protective material extending over the surface of said second film of transparent, plastic material opposite from said surface having said transparent, electrically conductive coating.

35. An incubator hood as recited in claim 34 wherein said transparent, electrically conductive coating is indium tin oxide.

* * * * *